(12) United States Patent
Flagle et al.

(10) Patent No.: US 7,717,951 B2
(45) Date of Patent: May 18, 2010

(54) DELIVERY SYSTEM THAT FACILITATES VISUAL INSPECTION OF AN INTRALUMINAL MEDICAL DEVICE

(75) Inventors: Jacob A. Flagle, Bloomington, IN (US); Brian C. Case, Bloomington, IN (US); Andrew K. Hoffa, Bloomington, IN (US); Michael L. Garrison, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 945 days.

(21) Appl. No.: 11/123,312

(22) Filed: May 6, 2005

(65) Prior Publication Data

US 2005/0283178 A1    Dec. 22, 2005

Related U.S. Application Data

(60) Provisional application No. 60/568,775, filed on May 6, 2004.

(51) Int. Cl.
    *A61F 2/84* (2006.01)
(52) U.S. Cl. .................. 623/1.23; 623/2.11; 623/1.11
(58) Field of Classification Search ............. 606/108, 606/190, 191, 194, 198, 192; 623/1.11, 1.12, 623/1.23, 1.34, 2.17, 1.24–1.26, 2.11
    See application file for complete search history.

(56) References Cited

U.S. PATENT DOCUMENTS

| | | | |
|---|---|---|---|
| 3,978,863 A * | 9/1976 | Fettel et al. ................ 606/194 |
| 5,234,411 A | 8/1993 | Vaillancourt | |
| 5,415,634 A * | 5/1995 | Glynn et al. ........... 604/103.08 |
| 5,486,193 A * | 1/1996 | Bourne et al. .............. 606/194 |
| 5,609,598 A | 3/1997 | Laufer et al. | |
| 5,810,847 A | 9/1998 | Laufer et al. | |
| 5,817,100 A | 10/1998 | Igaki | |
| 5,840,081 A * | 11/1998 | Andersen et al. .......... 623/1.11 |
| 5,902,247 A | 5/1999 | Coe et al. | |
| 5,911,452 A | 6/1999 | Yan | |
| 5,968,052 A | 10/1999 | Sullivan, III et al. | |
| 6,093,194 A | 7/2000 | Mikus et al. | |
| 6,221,081 B1 | 4/2001 | Mikus et al. | |
| 6,287,315 B1 | 9/2001 | Wijeratne et al. | |
| 6,413,269 B1 | 7/2002 | Bui et al. | |
| 6,475,168 B1 * | 11/2002 | Pugsley et al. ............. 600/585 |
| 6,554,848 B2 * | 4/2003 | Boylan et al. .............. 606/191 |
| 6,726,712 B1 | 4/2004 | Raeder-Devens et al. | |

(Continued)

FOREIGN PATENT DOCUMENTS

EP    1 016 422 A    7/2000

(Continued)

OTHER PUBLICATIONS

Thermedics Polymer Products Brochure, a division of VIASYS Healthcare—Selection Guide p. 6—"Radiopacifiers", pp. 8. Copyright © 2000-2008.

*Primary Examiner*—Anhtuan T Nguyen
*Assistant Examiner*—Ryan J Severson
(74) *Attorney, Agent, or Firm*—Buchanan Intellectual Property Office LLC

(57) ABSTRACT

Delivery systems, methods of making delivery systems, and methods of treatment are provided. A delivery system according to the invention facilitates a visual inspection of an intraluminal medical device included in the delivery system.

4 Claims, 5 Drawing Sheets

U.S. PATENT DOCUMENTS

| | | |
|---|---|---|
| 6,796,976 B1 | 9/2004 | Chin et al. |
| 6,942,688 B2 | 9/2005 | Bartholf et al. |
| 2001/0010017 A1 | 7/2001 | Letac et al. |
| 2001/0034549 A1 | 10/2001 | Bartholf et al. |
| 2001/0049549 A1 | 12/2001 | Boylan et al. |
| 2002/0193863 A1* | 12/2002 | Rourke et al. ............... 623/1.11 |
| 2003/0050686 A1 | 3/2003 | Raeder-Devens et al. |
| 2003/0055492 A1* | 3/2003 | Shaolian et al. ............ 623/1.24 |
| 2003/0199963 A1 | 10/2003 | Tower et al. |

FOREIGN PATENT DOCUMENTS

| | | |
|---|---|---|
| EP | 1016422 | 7/2000 |
| WO | WO/02/22053 | 3/2002 |
| WO | WO 02/22053 A | 3/2002 |

* cited by examiner

DELIVERY SYSTEM THAT FACILITATES VISUAL INSPECTION OF AN INTRALUMINAL MEDICAL DEVICE

CROSS REFERENCE TO RELATED APPLICATION

This application claims priority to U.S. Provisional Application Ser. No. 60/568,775 filed on May 6, 2004. The entire disclosure of which is hereby incorporated into this disclosure in its entirety.

FIELD OF THE INVENTION

The present invention relates to medical devices. More particularly, the invention relates to a delivery system for implantation of an intraluminal medical device in a body vessel.

BACKGROUND

Minimally invasive techniques and instruments for placement of intraluminal medical devices have been developed over recent years and are frequently used to deliver an intraluminal medical device to a desired point of treatment and deploy the intraluminal medical device at the point of treatment. In these techniques, a delivery system is used to carry the intraluminal medical device through a body vessel and to the point of treatment. Once the point of treatment is reached, the intraluminal medical device is deployed from the delivery system. The delivery system is subsequently withdrawn from the point of treatment and, ultimately, the body vessel. A wide variety of treatment devices that utilize minimally invasive technology have been developed and include stents, stent grafts, occlusion devices, infusion catheters, prosthetic valves, and the like.

Some intraluminal medical devices include a component that requires pre-treatment processing by a care provider or other personnel. For example, some prosthetic venous valves include a graft member that requires hydration prior to implantation. The hydration can be accomplished while the device is still in the delivery system. Also, some intraluminal medical devices, such as prosthetic valves, include a functional mechanism which is sensitive to positioning in the body vessel. For example, prosthetic venous valves may include a valve orifice that is desirably positioned within a body vessel in a particular orientation. For these devices, it can be important to achieve a desired positioning of the medical device within a delivery system during manufacturing.

Accordingly, there is a need for a delivery system which facilitates visual inspection of an intraluminal medical device within the delivery system.

SUMMARY OF EXEMPLARY EMBODIMENTS OF THE INVENTION

The invention provides delivery systems for delivering an intraluminal medical device to a point of treatment in a body vessel. Delivery systems according to the invention facilitate inspection of the intraluminal medical device placed within the delivery system.

In one embodiment, a delivery system according to the invention comprises an elongate tubular member having a distal end adapted for insertion into a body vessel. At least a portion of the tubular member is formed of a transparent material or a translucent material. The delivery system also includes a dilator having a distal end adapted for insertion into the body vessel. The dilator is disposed in the tubular member and extends substantially coaxially with the tubular member. An intraluminal medical device is disposed radially between the tubular member and the dilator. At least a portion of the intraluminal medical device is viewable through the portion of the tubular member formed of the transparent material or the translucent material.

In another embodiment, a delivery system according to the invention comprises an elongate tubular member having a distal end adapted for insertion into a body vessel. At least a portion of the tubular member is formed of a transparent material. The delivery system also includes a dilator disposed in the tubular member and extending substantially coaxially with the tubular member. The dilator has a lumen formed therein adapted to receive a guide wire. An intraluminal medical device is disposed radially between the tubular member and the dilator and has at least a portion thereof viewable through the portion of the tubular member formed of the transparent material. The tubular member includes at least one marker adjacent the distal end thereof.

In another embodiment, a delivery system according to the invention comprises an elongate tubular member having a distal end adapted for insertion into a body vessel. At least a portion of the tubular member is formed of a translucent material. The delivery system also includes a dilator disposed in the tubular member and extending substantially coaxially with the tubular member. The dilator has a lumen formed therein adapted to receive a guide wire. An intraluminal medical device is disposed radially between the tubular member and the dilator and has at least a portion thereof viewable through the portion of the tubular member formed of the translucent material. The tubular member includes at least one marker adjacent the distal end thereof.

In another embodiment, a delivery system according to the invention comprises an elongate tubular member having a distal end adapted for insertion into a body vessel. At least a portion of the tubular member is formed of a transparent material or a translucent material. The delivery system also includes a dilator disposed in the tubular member and extending substantially coaxially with the tubular member. The dilator has a lumen formed therein adapted to receive a guide wire. An intraluminal medical device is disposed radially between the tubular member and the dilator and has at least a portion thereof viewable through the portion of the tubular member formed of the transparent material or the translucent material. The tubular member includes at least one marker on the portion of the tubular member formed of the transparent material or the translucent material. The marker can facilitate a positioning of the intraluminal medical device within the body vessel.

The invention also provides methods of producing a delivery system.

One method according to the invention comprises the steps of forming a tubular member having at least a portion thereof which is translucent or transparent. A dilator is caused to be substantially disposed in the tubular member. An intraluminal medical device is inserted at a distal end of the tubular member radially between the tubular member and the dilator with at least a portion thereof viewable through the translucent and transparent portion of the tubular member.

DETAILED DESCRIPTION OF EXEMPLARY EMBODIMENTS OF THE INVENTION

The following detailed description and appended drawings describe and illustrate various exemplary embodiments of the invention. The description and drawings serve to enable one skilled in the art to make and use the invention, and are not intended to limit the scope of the invention in any manner.

Figure 6:
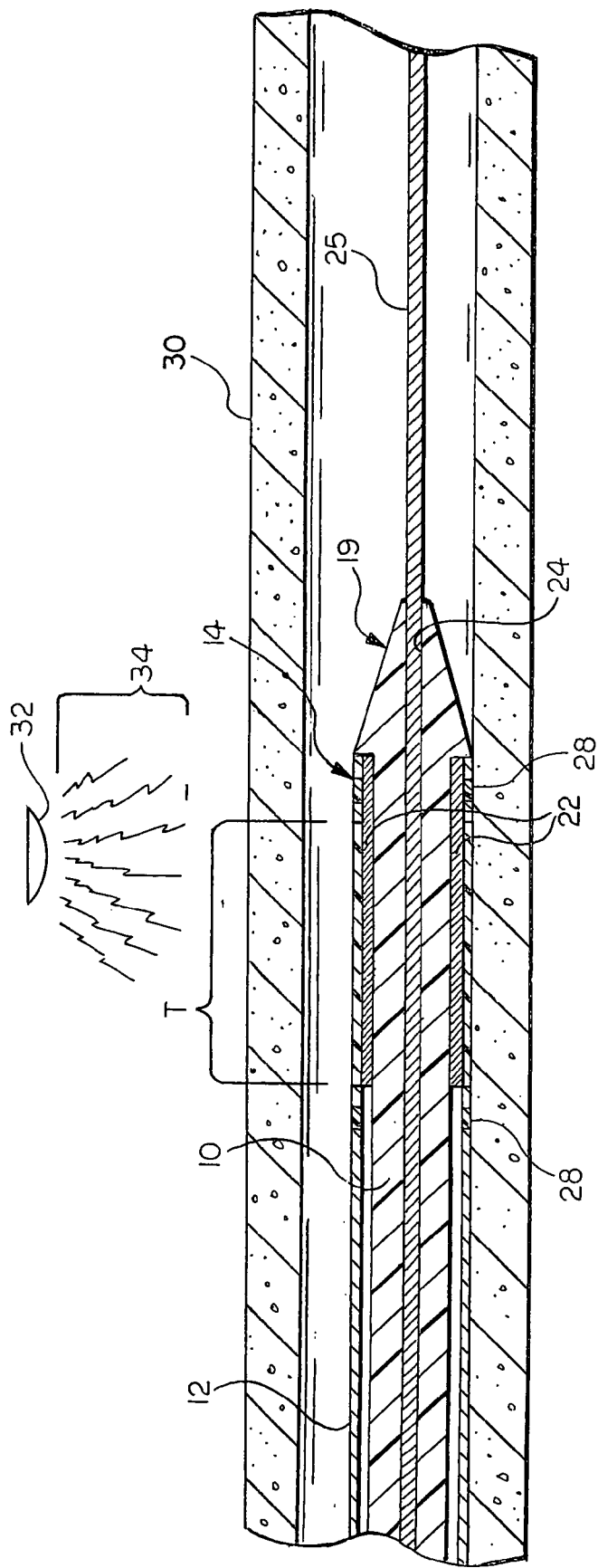
FIG. 6 is a schematic sectional view of the delivery system of FIG. 1 shown inserted in a body vessel.

FIGS. 1, 2, 3, 4 and 6 illustrate a delivery system 10 according to one embodiment of the invention. The delivery system 10 includes an elongate sheath or tubular member 12 having a distal end 14 which is insertable in a body vessel 30 as shown in FIG. 6 and a proximal end 16 that can be coupled to a connector 18; such as a Touhy Borst adapter. The tubular member 12 is formed of a flexible material, such as polytetrafluoroethylene or other suitable polymeric material, for example. The tubular member 12 includes an axial portion T of the length thereof formed of a transparent material. It is understood that the portion T of the tubular member 12 could be formed of a translucent material without departing from the scope and spirit of the invention. It is also understood that the length of the portion T can be varied as desired. Further, the degree of translucence can be controlled by use of known translucent materials or by balancing a ratio of the translucent material and a radiopacifier.

The delivery system 10 includes a dilator 20 disposed within the tubular member 12. As used herein, the term "dilator" refers to an elongate member capable of being disposed within a lumen of a sheath, such as tubular member 12. The dilator 20 has a tapered distal end 19, which is insertable in the body vessel 30 and a proximal end 21. An expandable intraluminal medical device 22 is disposed around a portion of the dilator 20 adjacent the distal end 19. The intraluminal medical device 22 may be any suitable intraluminal medical device, examples of which include a stent, a prosthetic valve, a filter, and the like. Further, the intraluminal medical device 22 can be a self-expandable device or a device that requires an input of force for expansion, such as a balloon-expandable device.

Figure 1:
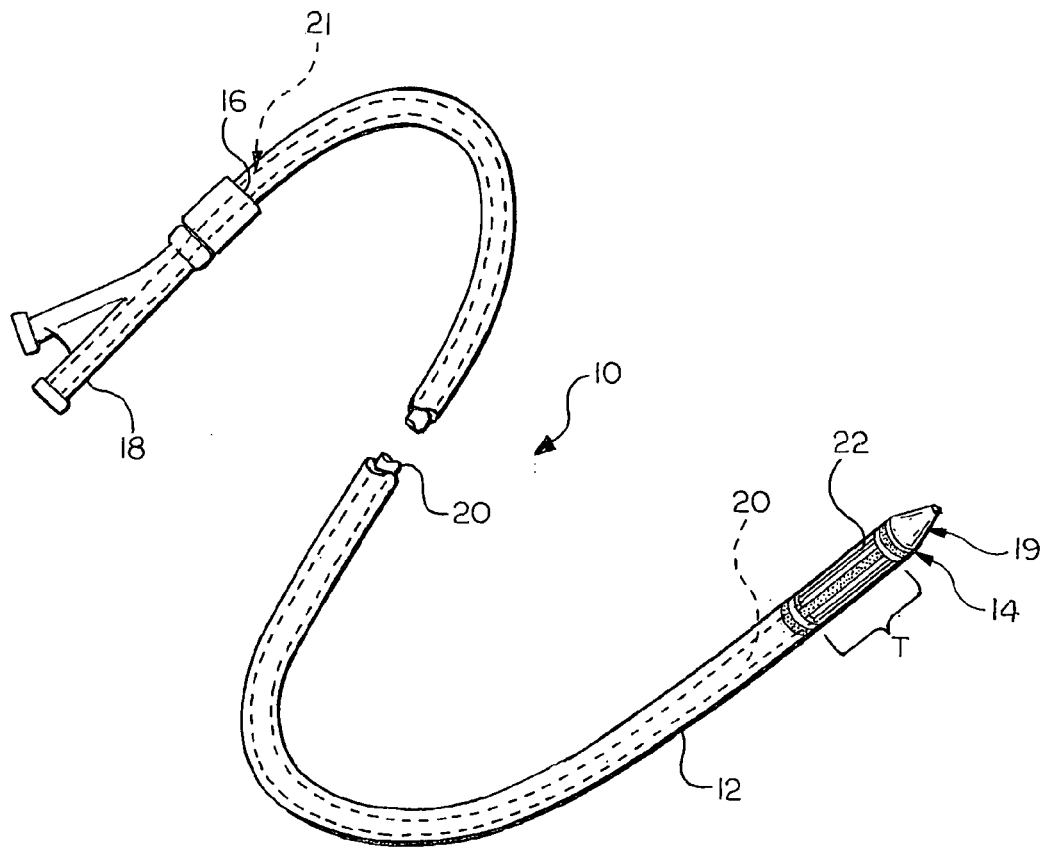
FIG. 1 is a perspective view of a delivery system according to one embodiment of the invention.
Figure 2:
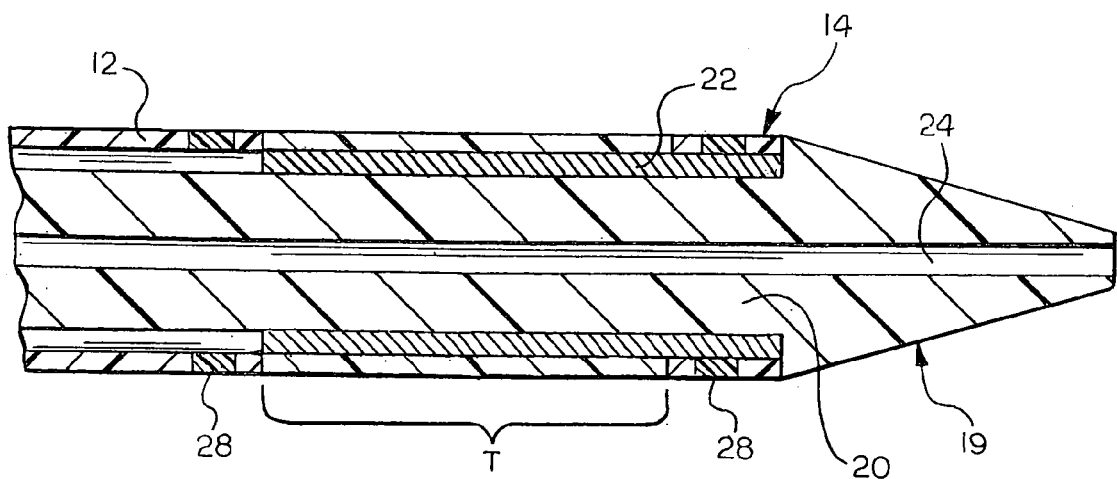
FIG. 2 is a sectional view of the distal end of the delivery system illustrated in FIG. 1.

FIG. 2 illustrates the distal end of the delivery system 10, illustrated in FIG. 1, including the distal end 14 of the tubular member 12 and the distal end 19 of the dilator 20. A lumen 24 is formed by the dilator 20 and extends along the entire length of the dilator 20. The lumen 24 is adapted to receive a guidewire, such as guidewire 25 shown in FIG. 6 or any other suitable member, therein. The lumen 24 may aid in the implanting of the intraluminal medical device 22 or carry other medical devices to the distal end 19 during insertion in the body vessel 30.

Figure 3:
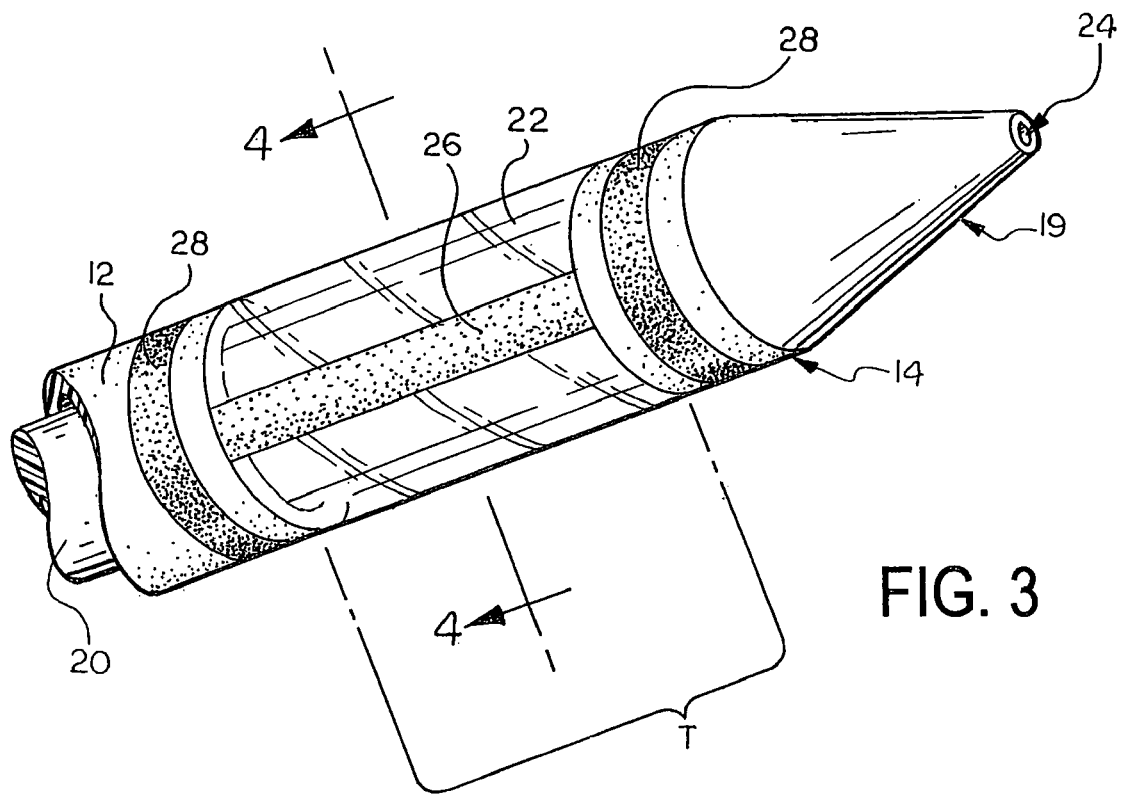
FIG. 3 is a perspective view of the distal end of the delivery system illustrated in FIGS. 1 and 2.

FIG. 3 illustrates the distal end 14 of the tubular member 12 and the distal end 19 of the dilator 20 illustrated in FIGS. 1 and 2. A longitudinal marker or radiopacifier 26 is formed in the transparent section T of the tubular member 12. The longitudinal marker 26 can be formed of any conventional radiopacifier material such as barium sulfate, bismuth salts, bismuth subcarbonate, tungsten, or tungsten powder, for example. The radiopacifier material used to form the longitudinal marker 26 may be detectable by fluoroscopy and X-ray, for example. Also, the longitudinal marker 26 can be formed in, with, or on the tubular member 12. The longitudinal marker 26, and indeed all markers used in delivery systems according to the invention, can be associated with the tubular member 12 in any suitable manner. Examples of suitable techniques include coextruding the material of the marker 26 with the material of the tubular member 12, physically embedding the material of the marker 26 into the material of the tubular member 12, and applying the material of the marker 26 to the material of the tubular member 12, such as on an interior or exterior surface. Any number and arrangement of longitudinal markers 26, such as an annular array, for example, can be associated with the tubular member 12 as desired without departing from the scope and spirit of the invention.

In the illustrated embodiment, a circumferential marker or radiopacifier 28 is formed at each end of the transparent section T of the tubular member 12. As used herein, the term "circumferential" refers to a marker that extends along at least a portion of a circumference of the tubular member. The term includes, but does not require, a marker that extends along the entire circumference of the member. Similar to the longitudinal marker 26, the circumferential marker 28 can be formed of any conventional radiopacifier material such as barium sulfate, bismuth salts, bismuth subcarbonate, tungsten, or tungsten powder, for example. The radiopacifier material used to form the circumferential marker 28 may be detectable by fluoroscopy and X-ray, for example. Also similar to the longitudinal marker 26, the circumferential marker 28 can be formed in, with, or on the tubular member 12. It is understood that a single circumferential marker 28 may be used at either end of the transparent section T or elsewhere on the tubular member 12, as desired.

Figure 4:
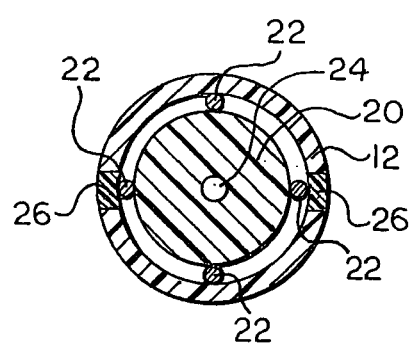
FIG. 4 is a sectional view of the delivery system illustrated in FIG. 3, taken along line 4-4.
Figure 5:
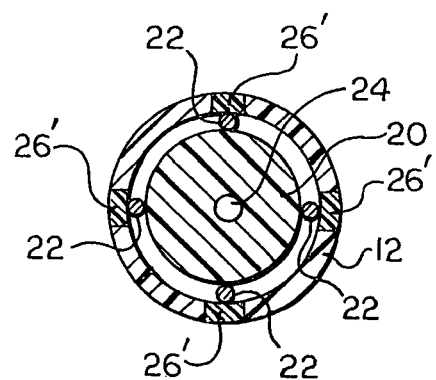
FIG. 5 is a sectional view of an alternate embodiment of the delivery system of FIGS. 1-3.

As best shown in FIG. 4, the illustrated embodiment includes two longitudinal markers 26 formed 180 degrees apart from each other. FIG. 5 illustrates an alternate embodiment that includes four longitudinal markers 26' circumferentially formed 90 degrees apart. It will be appreciated that in the embodiments illustrated, the longitudinal markers 26, 26' of FIGS. 4 and 5 are axially aligned with longitudinal portions of the intraluminal medical device 22. Thus, a user can know the orientation of the intraluminal medical device 22 within a body vessel of a patient by using a visualization technique, such as fluoroscopy, to view the longitudinal markers 26, 26' once the orientation of the intraluminal medical device 22 relative to the longitudinal markers 26, 26' is known. This information can be obtained prior to insertion of the delivery system into the body vessel by visually inspecting the intraluminal medical device through the transparent or translucent portion T.

It is understood that more or fewer longitudinal markers can be used as desired with intraluminal medical devices 22 having different configurations than that illustrated to facilitate observing the orientation thereof. Also, it is understood that markers having different configurations than those illustrated, such as helical and spot markers, for example, can be used. The various markers can be used for determining the axial location of the intraluminal medical device 22 in respect of the desired area of treatment within the body of the patient. A rotational orientation of the intraluminal medical device can also be determined using the markers. For example, a prosthetic valve can be disposed in the delivery system and oriented so that markers are disposed adjacent two sides of a valve orifice. Therefore, after insertion in the body vessel 30, confirmation of the rotational orientation of the valve orifice can be determined. This can be understood by observing FIG. 4, wherein the markers 26 are oriented adjacent the side portions of the intraluminal medical device 22. If the entire delivery system 10 is rotated within a body vessel, the side portions of the intraluminal medical device 22 are rotated and maintain alignment with the markers 26. The valve orifice may be aligned with the side portions on the prosthetic valve, and thus, the current rotational alignment of the side portions and the valve orifice can be determined in the body vessel 30.

In FIG. 6, the distal end of the delivery system 10 is shown within a body vessel 30. A fluoroscopy source 32 is shown directing energy 34 on the portion of the body vessel 30 where the distal end 14 of the tubular member 12 is located. The markers 26, 28 previously described can be detected by the fluoroscopy source 32.

Figure 7:
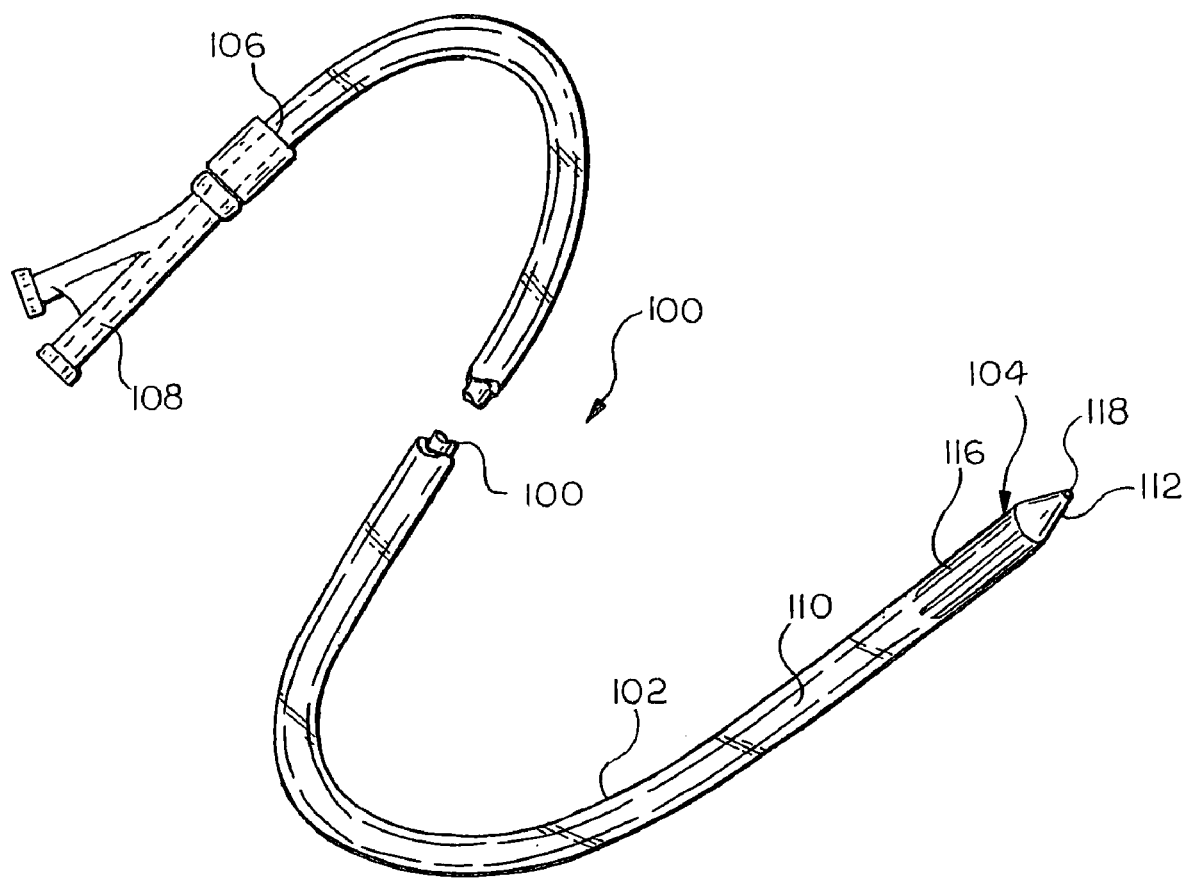
FIG. 7 is a perspective view of a delivery system according to another embodiment of the invention.

FIG. 7 shows a delivery system 100 according to another embodiment of the invention. In this embodiment, the delivery system 100 includes an elongate sheath or tubular member 102 having a distal end 104 and a proximal end 106 that can be coupled to a connector 108. The tubular member 102 is formed of a flexible transparent material over the entire length thereof. It is understood that the tubular member 102 could also be formed of a translucent material over its entire length without departing from the scope and spirit of the invention. The degree of translucence can be controlled by use of known translucent materials or by balancing a ratio of the translucent material and a radiopacifier.

The delivery device 100 includes a dilator 110 disposed within the tubular member 102. The dilator 110 has a tapered distal end 112, which is insertable in a body vessel, and a proximal end 114. An expandable intraluminal medical device 116 is disposed around a portion of the dilator 110 adjacent the distal end 112. The intraluminal medical device 116 may be any suitable intraluminal medical device, examples of which include a stent, a prosthetic valve, a filter, and the like.

A lumen 118 is formed by the dilator 110 and runs the entire length of the dilator 110. The lumen 118 is adapted to receive a guidewire or other insertable member therein like that discussed for the embodiment shown in FIGS. 1, 2, 3, 4 and 6. The lumen 118 may aid in the implanting of an intraluminal medical device or carry other medical devices to the distal end 112 during insertion in a body vessel.

Markers or radiopacifiers can be formed in, with, or on the tubular member 102 in similar fashion as described above for other embodiments of the invention. The markers can be formed at any point on the tubular member 102 and in any configuration as desired to function as described for the embodiments discussed above, and can be formed of any conventional radiopacifier material such as barium sulfate, bismuth salts, bismuth subcarbonate, tungsten, or tungsten powder, for example. The radiopacifier material used to form the markers may be detectable by fluoroscopy and X-ray, for example.

Both delivery systems 10, 100 can be used in the same manner. Therefore, an exemplary use of the delivery system 10 will be disclosed. It is understood, however, that the delivery system 100 can be similarly used, as can all delivery systems according to the invention. In use, the delivery system 10 delivers the intraluminal medical device 22 to a desired location within the body vessel 30. To deliver the intraluminal medical device 22, the guidewire 25 is placed in the body vessel 30 of the patient by navigating a distal end of the guidewire 25 to a point just beyond the desired area of treatment. A proximal end of the guidewire 25 is left outside the body of the patient.

The delivery system 10 is provided with the intraluminal medical device 22 disposed therein. Prior to insertion of the delivery system 10 into the body vessel, certain procedures may be accomplished and facilitated using the transparent or translucent portion of the tubular member 12. For example, the intraluminal medical device 22 can be inspected prior to its use. Additionally, certain intraluminal medical devices may include a component that requires pre-treatment processing by a care provider. Some prosthetic valves having leaflets or graft members, for example, may require hydration prior to implanting in the body vessel 30. The hydration can be accomplished in the tubular member 12 while the device is still in the delivery system 10. Hydration of the intraluminal medical device 22 can be verified by examining the intraluminal medical device 22 through the transparent or translucent portion T of the tubular member 12. The care provider can also inspect the delivery system 10 for undesirable air bubbles and the like through the transparent or translucent portion T. Other pre-insertion procedures facilitated by the transparent or translucent portion T of the tubular member 12 can be conducted as desired.

When it is desired to insert the delivery system 10 in the body vessel 30, the proximal end of the guidewire 25 is inserted into the lumen 24 of the dilator 20 at the distal end 19. The distal end 19 of the dilator 20 is caused to enter the body vessel 30 along the guidewire 25 and to be moved to the desired area of treatment. Progress through the body vessel 30 of the distal end 19 of the dilator 20 and the distal end 14 of the tubular member 12 can be tracked using the fluoroscopy source 32. The markers 26, 26', 28 are visible in conjunction with the fluoroscopy source 32, thus facilitating the tracking of the distal ends 19, 14. An axial and rotational orientation of the intraluminal medical device 22 can be monitored within the body vessel 30 using the fluoroscopy source 32. Thus, a desired axial and rotational alignment of the intraluminal medical device 22 can be achieved by observing and recording the orientation of the intraluminal medical device 22 with respect to the longitudinal markers 26 outside of the patient's body, then causing a desired alignment to occur in the body vessel 30 using the fluoroscopy source 32.

Figure 8:
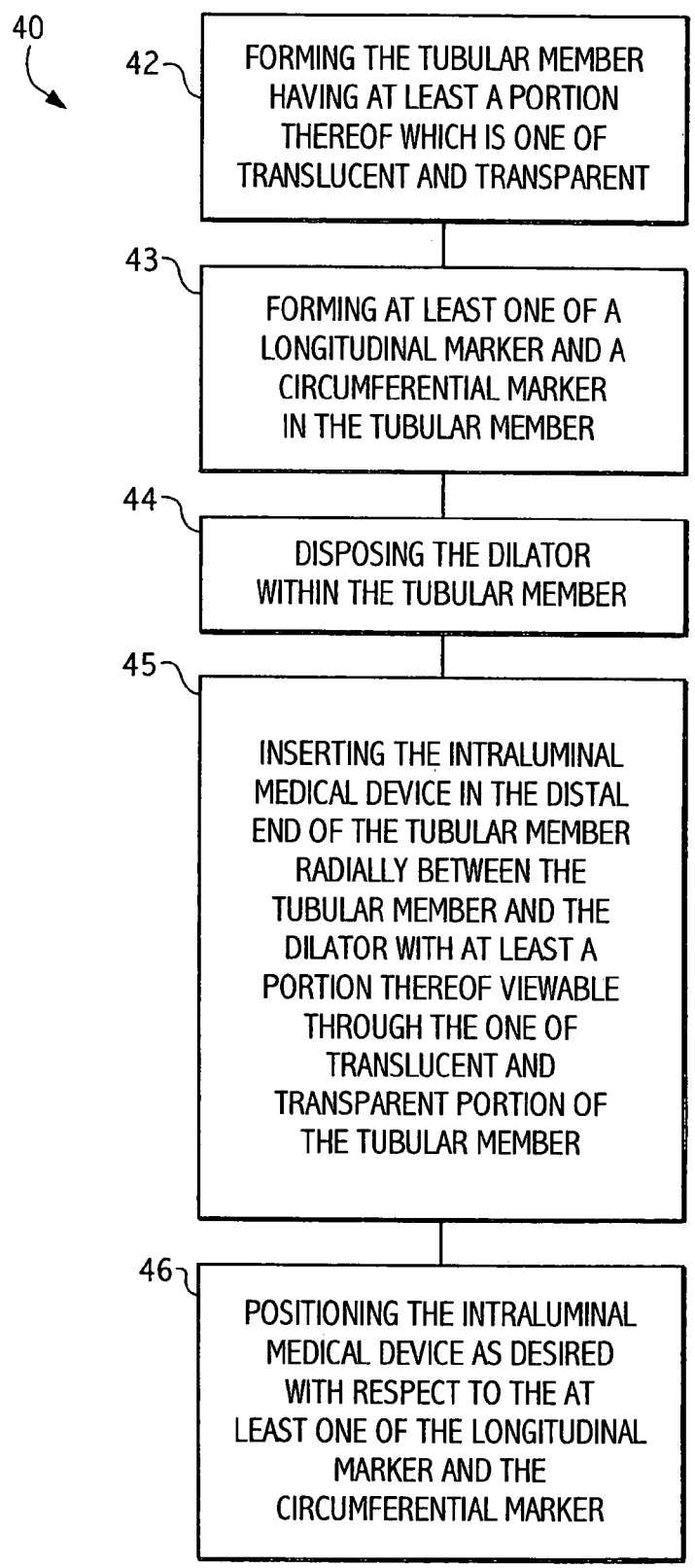
FIG. 8 is a flow diagram illustrating a method of producing a delivery system according to the invention.

FIG. 8 provides a flow diagram illustrating a method 40 of producing the delivery systems according to the invention. The steps presented are exemplary in nature, and thus, the order is not necessary or critical. In one step 42, the tubular member is formed having at least a portion thereof which is one of translucent and transparent. In another step 43, at least one of a longitudinal marker and a circumferential marker is formed in, with, or on the tubular member. The markers are formed in a desired location to facilitate observation thereof in the body of the patient. In another step 44, the dilator is inserted in the tubular member to be substantially coaxial therewith. In another step 45, the intraluminal medical device is inserted adjacent the distal end of the tubular member radially between the tubular member and the dilator with at least a portion thereof viewable through the one of the translucent and transparent portion of the tubular member. In another step 46, the intraluminal medical device is positioned as desired with respect to the at least one of the longitudinal marker and the circumferential marker. It is understood that all steps, and particularly steps 44 and 45, can be performed in any order. The method can include any further steps necessary to produce a desired finished delivery system, such as attaching any suitable connectors, adapters, and the like on various components of the delivery system.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. An intraluminal medical device delivery system comprising:
    an elongate tubular member having a distal end adapted for insertion into a body vessel, at least a portion of said tubular member being formed of one of a transparent material and a translucent material;
    a dilator disposed in said tubular member and substantially coaxial with said tubular member, said dilator having a lumen formed therein adapted to receive a guide wire;
    an intraluminal medical device disposed radially between said tubular member and said dilator and having at least a portion thereof viewable through the at least a portion of said tubular member formed of the one of a transparent material and a translucent material, the intraluminal medical device being separable from said delivery system and adapted to be deployed from said delivery system and implanted within a body vessel after being carried to a point of treatment in the body vessel by said delivery system;
    at least one longitudinal marker formed on said tubular member on the at least a portion of said tubular member formed of the one of a transparent material and a translucent material; and
    at least one circumferential marker formed on said tubular member and adjacent the at least a portion of said tubular member formed of the one of a transparent material and a translucent material but not on the portion;
    wherein the intraluminal medical device includes a longitudinal portion;
    wherein the at least one longitudinal marker is axially aligned with the longitudinal portion;
    wherein the intaluminal medical device comprises a prosthetic valve having a valve orifice; and
    wherein the at least one longitudinal marker is disposed adjacent the valve orifice.

2. The intraluminal medical device delivery system of claim 1, wherein the at least one longitudinal marker comprises two or more longitudinal markers; and
    wherein at least two of the at least two or more longitudinal markers are disposed adjacent the valve orifice.

3. An intraluminal medical device delivery system comprising:
    an elongate tubular member having a distal end adapted for insertion into a body vessel, a distal window portion of said tubular member being formed of one of a transparent material and a translucent material;
    a dilator disposed in said tubular member and substantially coaxial with said tubular member, said dilator having a lumen formed therein adapted to receive a guide wire;
    a prosthetic valve disposed radially between said tubular member and said dilator and having at least a portion thereof viewable through the distal window portion of said elongate tubular member, the prosthetic valve having a valve orifice and being separable from said delivery system and adapted to be deployed from said delivery system and implanted within a body vessel after being carried to a point of treatment in the body vessel by said delivery system;
    at least one longitudinal marker formed on said tubular member on the distal window portion; and
    at least one circumferential marker formed on said tubular member adjacent the distal window portion but not on the distal window portion;
    wherein the at least one longitudinal marker comprises two or more longitudinal markers; and
    wherein at least two of the at least two or more longitudinal markers are disposed adjacent the valve orifice.

4. An intraluminal medical device delivery system comprising:
    an elongate tubular member having a distal end adapted for insertion into a body vessel, a distal window portion of said tubular member being formed of one of a transparent material and a translucent material, the distal window portion having first and second ends;
    a dilator disposed in said tubular member and substantially coaxial with said tubular member, said dilator having a lumen formed therein adapted to receive a guide wire;
    a prosthetic valve disposed radially between said tubular member and said dilator and having at least a portion thereof viewable through the distal window portion of said elongate tubular member, the prosthetic valve having a valve orifice and being separable from said delivery system and adapted to be deployed from said delivery system and implanted within a body vessel after being carried to a point of treatment in the body vessel by said delivery system;
    at least one longitudinal marker formed on said tubular member on the distal window portion and disposed adjacent the valve orifice; and
    at least one circumferential marker disposed adjacent one of the first and second ends of the distal window portion of said elongate tubular member but not on the distal window portion.

* * * * *